United States Patent
Vamvakides et al.

(10) Patent No.: US 9,750,746 B2
(45) Date of Patent: Sep. 5, 2017

(54) ANAVEX2-73 AND CERTAIN ANTICHOLINESTERASE INHIBITORS COMPOSITION AND METHOD FOR NEUROPROTECTION

(71) Applicant: ANAVEX LIFE SCIENCES CORP, New York, NY (US)

(72) Inventors: Alexandre Vamvakides, Ymittos Attikis (GR); Tangui Maurice, Saint Gely-du-Fesc (FR)

(73) Assignee: Anavex Life Sciences Corp., New York, NY (US)

(*) Notice: Subject to any disclaimer, the term of this patent is extended or adjusted under 35 U.S.C. 154(b) by 447 days.

(21) Appl. No.: 13/940,352

(22) Filed: Jul. 12, 2013

(65) Prior Publication Data

US 2014/0296211 A1 Oct. 2, 2014

Related U.S. Application Data

(63) Continuation-in-part of application No. PCT/GR2013/000018, filed on Apr. 3, 2013.

(30) Foreign Application Priority Data

Mar. 28, 2013 (GR) ............... 20130100181

(51) Int. Cl.
| | |
|---|---|
| *A61K 31/34* | (2006.01) |
| *A61K 31/435* | (2006.01) |
| *A61K 31/44* | (2006.01) |
| *A61K 31/445* | (2006.01) |
| *A61K 31/55* | (2006.01) |
| *A61K 31/13* | (2006.01) |
| *A61K 31/27* | (2006.01) |
| *A61K 31/341* | (2006.01) |

(52) U.S. Cl.
CPC ............. *A61K 31/55* (2013.01); *A61K 31/13* (2013.01); *A61K 31/27* (2013.01); *A61K 31/34* (2013.01); *A61K 31/341* (2013.01); *A61K 31/435* (2013.01); *A61K 31/44* (2013.01); *A61K 31/445* (2013.01)

(58) Field of Classification Search
CPC ...... A61K 31/34; A61K 31/435; A61K 31/44; A61K 31/445
See application file for complete search history.

(56) References Cited

PUBLICATIONS

Villard et al. ("Anti-amnesic and neuroprotective potentials of the mixed muscarinic receptor/sigmal (σ1) ligand ANAVEX2-73, a novel aminotetrahydrofuran derivative" Journal of Psychopharmacology, 2011, 25(8), 1101-1117).*

Maurice "Protection by sigma-1-receptor agonists is synergic with donepezil, but not with memantine, in a mouse model of amyloid-induced memory impairments" Behavioural Brain Research, 2016, 296, 270-278.*

Espallergues, J. et al., "Involvement of the sigma1 receptor in the anti-amnesic, but not antidepressant-like, effects of the aminotetrahydrofuran derivative ANAVEX1-41", British Journal of Pharmacology (2007) 152, 267-279.

Villard, V. et al., "Antiamnesic and Neuroprotective Effects of the Aminotetraphydrofuran Derivative ANAVEX1-41 Against Amyloid Beta25-35-Induced Toxicity in Mice", Neuropsychopharmacology (2009) 34, 1552-1566.

Maurice, T. et al., "Amnesia induced in mice by centrally administered Beta-amyloid peptides involves cholinergic dysfunction", Brain Research 706 (1996) 181-193.

Zussy, C. et al., "Time-Course and Regional Analyses of the Physiopathological Changes Induced after Cerebral Injection of an Amyloid Beta Fragment in Rats", The American Journal of Pathology vol. 179, No. 1 Jul. 2011.

Hayashi, T. et al., "Sigma-1 Receptor Chaperones at the ER-Mitochondrion Interface Regulate Ca2+ Signaling and Cell Survival", Cell 131 596-610 Nov. 2007.

Meunier, J. et al., "The anti-amnesic and neuroprotective effects of donepezil against amyloid Beta25-35 peptide-induced toxicity in mice involve an interaction with the sigma1 receptor", British Journal of Pharmacology (2006) 149 998-1012.

Dovey, H. F. et al., "Functional gamma-secretase inhibitors reduce beta-amyloid peptide levels in brain", Journal of Neurochemistry 76 173-181.

Su, T. et al., "The sigma-1 receptor chaperone as an inter-organelle signaling modulator", Trends in Pharmacological Sciences, vol. 31, No. 12, 2010.

Vamvakides, A., "[Anticonvulsant and forced swin anti-immobility effects of tetrahydro-N, N-dimethyl-2, 2-diphenyl-3-furanemethanamine (AE37): common action mechanism]", Ann Pharm Fr. Mar. 2002; 60(2): 88-92, Abstract.

Vamvakides, A., "[Mechanism of action of tetrahydro-N, N-dimethyl-5, 5-dephenyl-3-furanemethanamine, a putative nootropic, anti-epileptic and antidepressant compound]", Ann Pharm Fr. Nov. 2002 60(6): 415-22, Abstract.

* cited by examiner

*Primary Examiner* — Yong Chong
(74) *Attorney, Agent, or Firm* — Polsinelli, PC (57) ABSTRACT

This invention concerns a dosage form comprising a therapeutically neuroprotective amount of A2-73 and a neuroprotective amount of at least one cooperating acetylcholinesterase inhibitor selected from the group consisting of donepezil, galantamine, rivastigmine, or memantine and method of use.

2 Claims, 5 Drawing Sheets

ANAVEX2-73 AND CERTAIN ANTICHOLINESTERASE INHIBITORS COMPOSITION AND METHOD FOR NEUROPROTECTION

CROSS-REFERENCE TO RELATED APPLICATIONS

Applicants claim priority to PCT/GR 2013/0000018 filed Apr. 3, 2013, and to GR 20130100181 filed Mar. 28, 2013 (Vamvakides).

FIELD OF THE INVENTION

This invention concerns a dosage form comprising a therapeutically neuroprotective amount of A2-73 and a neuroprotective amount of at least one cooperating acetylcholinesterase inhibitor selected from the group consisting of donepezil, galantamine, rivastigmine, or memantine and method of use.

BACKGROUND

Tetrahydro-N,N-dimethyl-2,2-diphenyl-3-furanmethanamine hydrochloride (ANAVEX2-73, or A2-73) is a compound which is believed to bind to muscarinic acetylcholine and sigma-1 receptors with affinities in the low micromolar range. It has been reported that A2-73 showed neuroprotective potential against amyloid toxicity in mice. In particular, A2-73 has been reported as attenuating oxidative stress, caspases induction, cellular loss and learning and memory deficits observed in mice one week after the icy injection of an oligomeric preparation of amyloid $\beta_{25-35}$ peptide ($A\beta_{25-35}$) (Villard et al., J Psychopharmacol 2011). More recently, it has been reported that A2-73 blocked the $A\beta_{25-35}$-induced P-Akt decrease and P-GSK-3β increase, indicating activation of the PI3K neuroprotective pathway (Lahmy et al., Neuropsychopharmacology, 2013). In the dose-range tested, A2-73 attenuated the hyperphosphorylation of Tau on physiological epitopes (AT-8 antibody clone) and on pathological epitopes (AT-100 clone). ANAVEX2-73 also has been reported decreasing the $A\beta_{25-35}$-induced endogenous $A\beta_{1-42}$ seeding.

A series of aminotetrahydrofuran compounds have been reported as exhibiting anti-amnesic, anticonvulsant, antidepressant and neuroprotective activities.[1-4] Among them, tetrahydro-N,N-dimethyl-2,2-diphenyl-3-furanmethanamine hydrochloride (ANAVEX2-73) is a mixed muscarinic/$\sigma_1$ protein profile, but with better selectivity for the $\sigma_1$ subtype as compared with $\sigma_2$ sites.[1] Reported binding analyses showed an $IC_{50}=860$ nM for $\sigma_1$ and no affinity for $\sigma_2$ sites. Moreover, the screening profile showed micromolar affinities for muscarinic M1-M4 receptors ($IC_{50}=3.3$-$5.2$ μM), sodium channel site 2 ($IC_{50}=5.1$ μM), and NMDA receptors ($IC_{50}=8.0$ μM).

Reference is made to donepezil

Donepezil (or DPZ) is reported to be a centrally acting reversible acetylcholinesterase inhibitor. Its main therapeutic use is in the symptomatic palliative treatment of mild to moderate Alzheimer's disease.

Reference is made to Memantine

Memantine is reported to act on the glutamatergic system by blocking NMDA-type glutamate receptors.

Reference is made to Galantamine

Galantamine is described as a competitive and reversible cholinesterase inhibitor.

Reference is made to Rivastigmine

Rivastigmine, an acetylcholinesterase inhibitor, believed to inhibit both butyrylcholinesterase and acetylcholinesterase.

Reference is made to the following publications, the teachings of which are incorporated by reference in their entirety.

[1] Vamvakides (2002) Ann Pharm Fr 60:88-92;
[2] Vamvakides (2002) Ann Pharm Fr 60:415-22;
[3] Espallergues et al. (2007) Br J Pharmacol 152:267-79;
[4] Villard et al (2009) Neuropsychopharmacology 34:1552-66;
[5] Maurice et al. (1996) Brain Res 706:181-93;
[6] Zussy et al. (2011) Am J Pathol 179:315-34;
[7] Hayashi & Su (2007) Cell 131:596-610;
[8] Su et al. (2010) Trends Pharmacol Sci 31:557-566;
[9] Meunier et al. (2006) Br J Pharmacol 149:998-1012.

Further noted are European Patent Application No. 08 702 158.0, "New Sigma-Receptor Ligands with Anti-Apoptotic and/or Pro-Apoptotic Properties Over Cellular Biochemical Mechanisms, With Neuroprotective, Anti-Cancer, Anti-Metastic and Anti-(Chronic) Inflammatory Action (also, U.S. Ser. No. 12/522,761), and U.S. Ser. No. 13/201,271, "Sigma Receptors Ligands With Anti-Apoptotic And/Or Pro-Apoptotic Properties, Over Cellular Dovey et al., Mechanisms, Exhibiting Prototypical Cytoprotective And Also Anticancer Activity, Journal of Neurochemistry, 76(1) 173-181 (2001). Functional gamma-secretase inhibitors reduce beta-amyloid peptide levels in brain All publications cited herein are incorporated by reference in their entirety.

SUMMARY OF THE INVENTION

The claimed invention concerns a dosage form comprising a therapeutically neuroprotective amount of A2-73 and a neuroprotective amount of at least one cooperating acetylcholinesterase inhibitor selected from the group consisting of donepezil, galantamine, rivastigmine, or memantine. Note is made of the dosage form having a neuroprotective amount of A2-73 from about 0.5 to about 20 mg.

In some embodiments, the at least one cooperating acetylcholinesterase inhibitor is donepezil, with reference to donepezil at from about 0.5 mg to about 23 mg, and particularly from about 0.5 mg to less than about 5 mg, and more particularly from about 1 to about 3.5 mg.

In other embodiments the at least one cooperating acetylcholinesterase inhibitor is galantamine, and particularly from about 0.5 mg to about 20 mg.

Attention is drawn to a dosage form wherein said at least one cooperating acetylcholinesterase inhibitor is rivastagmine, and particularly from about 0.5 mg to about 20 mg.

Further attention is drawn to the dosage form wherein said at least one cooperating acetylcholinesterase inhibitor is memantine, with particular reference to a neuroprotective amount of from about 0.5 mg to about 30 mg.

This invention further includes a therapeutic method of neuroprotection in a subject with actual or anticipated neuronal injury comprising administering a neuroprotective dose of A2-73 in conjunction with at least one neuroprotective dose selected from the group consisting of donepezil, galantamine, rivastigmine, or memantine. Note is made of the method employing a neuroprotective amount of A2-73 from about 0.5 to about 20 mg. Note is further made of co-timely administration of said neuroprotective dose of A2-73 in conjunction with at least one neuroprotective dose selected from the group consisting of donepezil, galantamine, rivastigmine, or memantine, and particularly where the dose or dosage form including donepezil, galantamine, rivastigmine, or memantine consists of a sub-MAD dose of donepezil, galantamine, rivastigmine, or memantine.

In some embodiments of the method, the at least one cooperating acetylcholinesterase inhibitor is donepezil, with reference to donepezil at from about 0.5 mg to about 23 mg, and particularly from about 0.5 mg to less than about 5 mg, and more particularly from about 1 to about 3.5 mg.

In other embodiments of the method the at least one cooperating acetylcholinesterase inhibitor is galantamine, and particularly from about 0.5 mg to about 20 mg.

Attention is drawn to the method wherein said at least one cooperating acetylcholinesterase inhibitor is rivastagmine, and particularly from about 0.5 mg to about 20 mg.

Further attention is drawn to the method wherein said at least one cooperating acetylcholinesterase inhibitor is memantine, with particular reference to a neuroprotective amount of from about 0.5 mg to about 30 mg.

BRIEF DESCRIPTION OF THE DRAWINGS

Administration schedule: mice received ANAVEX2-73 (0.1-1 mg/kg i.p.) once-a-day between days −7 and −1 and $A\beta_{25-35}$ (9 nmol i.c.v.) at day 0. Animals were examined between days 7 and 9. Their brain dissected out and assessed for lipid peroxidation (LPO) at day 10. $F_{(4,49)}=16.4$, $p<0.0001$ in (b); $H=6.9$, $p<0.01$ in (c); $F_{(4,2)}=53.9$, $p<0.001$ in (d); n=10 per group in (b,c) and 6 in (d). *$p<0.05$, **$p<0.01$ vs. the Sc.A$\beta$/V-treated group; # $p<0.05$, ## $p<0.01$ vs. the $A\beta_{25-35}$/V-treated group; Dunnett's test in (b, d); Dunn's test in (c).

Administration schedule: mice received $A\beta_{25-35}$ (9 nmol i.c.v.) at day 0 and ANAVEX2-73 (0.1, 0.3 mg/kg i.p.) once-a-day between days 7 and 13. Animals were examined between days 14 and 16. Their brain dissected out and assessed for lipid peroxidation (LPO) at day 17. $F_{(3,39)}=10.5$, $p<0.0001$ in (b); $H=10.3$, $p<0.05$ in (c); $F_{(3,23)}=3.45$, $p<0.05$ in (d); n=10 per group in (b, c) and 6 in (d). *$p<0.05$, **$p<0.01$ vs. the Sc.A$\beta$/V-treated group; # $p<0.05$, ## $p<0.01$ vs. the $A\beta_{25-35}$/V-treated group; Dunnett's test in (b, d); Dunn's test in (c).

DETAILED DESCRIPTION OF THE INVENTION

Without being bound by any particular theory it is believed that A2-73 acts as a disease-modifying or pathology-modifying agent not only protecting brain cells from toxicity but also contributing to decrease Tau pathology and amyloid load. Disclosed herein is the administration schedule and combination of A2-73 as a combination therapy with donepezil and/or memantine.

As used herein, the term "neuroprotection" shall mean the protecting of neurons in the brain, central nervous system or peripheral nervous system (preferably in the brain or spinal cord) from death and/or damage. Preferably, the neurons are protected from death or damage caused by oxidative stress, for example oxygen radicals.

More broadly, neuroprotection shall be understood to include protection or amelioration of neurological insult with particular reference to stroke, traumatic brain injury, and spinal cord injury, moderating or avoiding the pathologic metabolic cascades associated with stroke, traumatic brain injury and retinal damage as a result of glaucoma. In disclosed data, we have obtained evidence that the neuroprotective action of A2-73 is effective against:
- against amyloid toxicity
- oxidative stress,
- caspases induction,
- cellular loss,
- learning and memory deficits,
- deficit in endogenous neuroprotection factors (e.g. BDNF),
- decrease in protective kinase activities (e.g. AKT) or increase in deleterious kinase activities (e.g. GSK-3β),
- attenuation of hyperphosphorylation of Tau on physiological epitopes (AT-8 antibody clone) and on pathological epitopes (AT-100 clone).
- decrease the $A\beta_{25-35}$-induced endogenous $A\beta_{1-42}$ seeding.

ANAVEX2-73 (0.1, 0.3 mg/kg ip), administered once a day between day -7 and day -1 before $A\beta_{25-35}$ (day 0), blocked the $A\beta_{25-35}$-induced memory deficits (spontaneous alternation in the Y maze and passive avoidance response) and lipid peroxidation in the hippocampus 7 days after $A\beta_{25-35}$. ANAVEX2-73 (0.3 mg/kg ip) was also effective when it was administered once a day between day 7 and day 13 after $A\beta_{25-35}$ (on day 0), on memory deficits and lipid peroxidation increase measured 14 days after $A\beta_{25-35}$. In combination with donepezil (0.25, 0.5 mg/kg ip), the effects appeared synergistic, since the combination of the lowest non-effective doses (0.25 donepezil+0.1 ANAVEX2-73) led to a significant protection on all parameters examined.

The impact of administration schedule and combination of A2-73 with donepezil or memantine is disclosed.

The ANAVEX2-73 drug was administered at 0.1, 0.3 mg/kg ip once a day between day -7 and day -1 before $A\beta_{25-35}$ (day 0). It blocked the $A\beta_{25-35}$-induced memory deficits (spontaneous alternation in the Y maze and passive avoidance response) and lipid peroxidation in the hippocampus 7 days after $A\beta_{25-35}$. ANAVEX2-73 (0.3 mg/kg ip) was also effective when it was administered once a day between day 7 and day 13 after $A\beta_{25-35}$ (on day 0), on memory deficits and lipid peroxidation increase measured 14 days after $A\beta_{25-35}$.

Combination studies with memantine showed a therapeutic efficacy of memantine or A2-73 alone and similar efficacy when the compounds were used in combination.

The combination with donepezil engendered a synergistic effect. The minimal active dose of each drug (0.25 mg/kg for donepezil and 0.1 mg/kg for A2-73, led to therapeutic protection on all parameters examined. In combination with donepezil the combination showed an increased efficacy, similar to the most active drug in the mix. These results showed therapeutic utility in preventing and restoring efficacy for the compound in the $A\beta_{25-35}$ model in mice and a preserved efficacy in combination with the reference A2-73.

Materials and Methods

Animals

Male Swiss OF-1 mice (Depré, St Doulchard, France), aged 7-9 weeks and weighing 32±2 g were used in this study. Animals were housed in plastic cages in groups. They had free access to food and water, except during behavioral experiments, and they were kept in a regulated environment (23±1° C., 40-60% humidity) under a 12 h light/dark cycle (light on at 07:00 am). Experiments were carried out between 09:00 am and 05:00 pm, in an experimental room within the animal facility. Mice were habituated 30 min before each experiment. Animal procedures were conducted in adherence with the EU Directive 86-609.

Drugs and Administration Procedures

Tetrahydro-N,N-dimethyl-2,2-diphenyl-3-furanmethanamine hydrochloride (ANAVEX2-73) was synthesized in the laboratory (Anavex Life Sciences, Greece). Donepezil (E2020) was from Eisai Tsukuba Research Laboratories (Tsukuba, Japan) and memantine was from Sigma-Aldrich (St Quentin-Fallavier, France). Drugs were solubilized in physiological saline solution and administered intraperitoneally (i.p.) in a volume of 100 μl per 20 g body weight. The amyloid-β[25-35] ($A\beta_{25-35}$) and scrambled $\beta_{25-35}$ (Sc.Aβ) peptides from Genepep (France) were solubilized in distilled water at 3 mg/ml and stored at 20° C. until use. Peptides were aged at 37° C. for 4 days and injected i.c.v. (3 μl per mouse).

Spontaneous Alternation in te Y-maze

Spatial working memory was examined through the measure of spontaneous alternation performance in the Y-maze. Animals were allowed to explore the Y-shaped maze during 8 min and the number of alternations (consecutive exploration of the 3 arms) and total number of arms entered was recorded.

Step-Through Passive Avoidance

Contextual long-term memory was measured using the step-through type passive avoidance test. During training, animals were placed in the white compartment of the two-compartment apparatus. The step-through latency to enter the dark compartment was recorded and mice received an electric shock (0.1 mA, 3 s). During the retention session, performed 24 h after training, the step-through latency to enter the dark compartement and escape latency, to re-exit, were recorded.

Lipid Peroxidation Measures

Mouse hippocampus was homogenized in cold methanol, centrifuged at 1,000 g 5 min and supernatant collected. Homogenate was added to a solution of $FeSO_4$ 1 mM, $H_2SO_4$ 0.25 M, xylenol orange 1 mM and incubated for 30 min at RT. Absorbance was measured at 580 nm ($A_{580}1$), and 10 μl of cumene hydroperoxide (CHP) 1 mM was added and incubated for 30 min at RT. Absorbance was measured at 580 nm ($A_{580}2$). Lipid peroxidation was determined as CHP equivalents: CHP eq.=$A_{580}1/A_{580}2\times$[CHP (nmol)]× dilution, and expressed as percentage of the Sc.Aβ/V-treated group value.

Results

It has been reported that ANAVEX2-73 is effective in reversing the learning impairments observed one week after the intracerebroventricular injection (icv) injection of $A\beta_{25-35}$ peptide. In the rodent brain, $A\beta_{25-35}$ peptide induces biochemical changes, morphological alterations and behavioral impairments reminiscent of AD physiopathology.[4,5,6] ANAVEX2-73 administered before the $A\beta_{25-35}$ peptide prevented the appearance of $A\beta_{25-35}$-induced learning deficits at 30 µg/kg. Oxidative stress and hippocampal cell loss were also prevented at 0.3-1 mg/kg. Without being bound by any particular theory, it is believed that the observed anti-apoptotic and anti-oxidant activity of ANAVEX2-73 relies on both its muscarinic and $\sigma_1$ activities.

ANAVEX2-73 is effective in preventing or moderating the peptide, $A\beta_{25-35}$,-induced toxicity and learning impairments when it is injected during one week before the peptide. Post-peptide administration is not required. This pre-insult protection schedule triggers neuromodulatory mechanisms (believed to impact the muscarinic and $\sigma_1$ receptors) to therapeutically protect the brain from amyloid toxicity. Chronic activation of the $\sigma_1$ receptor has been shown to facilitate ER stress response and modify lipid rafts composition, sustaining long-term modifications in the cell physiology.[7,8]

ANAVEX2-73 is able to reverse the $A\beta_{25-35}$-induced toxicity and learning impairments when it is injected repeatedly one week after the peptide. This is a restorative effect of the compound, together with a delayed ability to reduce the toxic load in the brain. Without being bound by any particular theory, the protective pathways activated by muscarinic receptor (involving the PI3K/AKT and MAPK pathways), modulated by the $\sigma_1$ receptor activation are likely to be involved in these effects.

Figure 1:
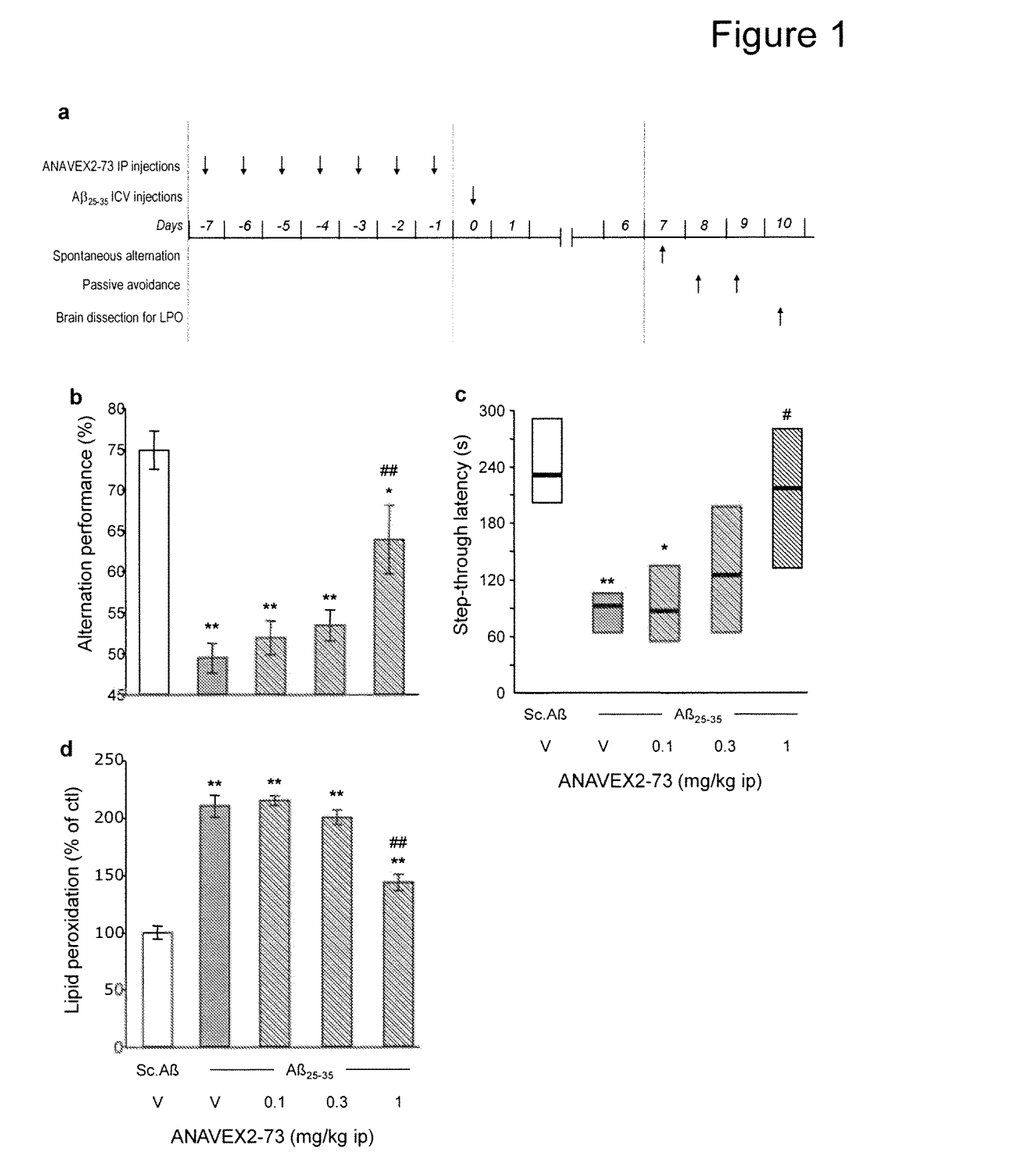
FIG. 1. Early administration of ANAVEX2-73 significantly prevented the $A\beta_{25-35}$-induced learning deficits and toxicity. (a) Administration schedule; (b) Y-maze test; (c) passive avoidance response and (d) lipid peroxidation measure.
Figure 2:
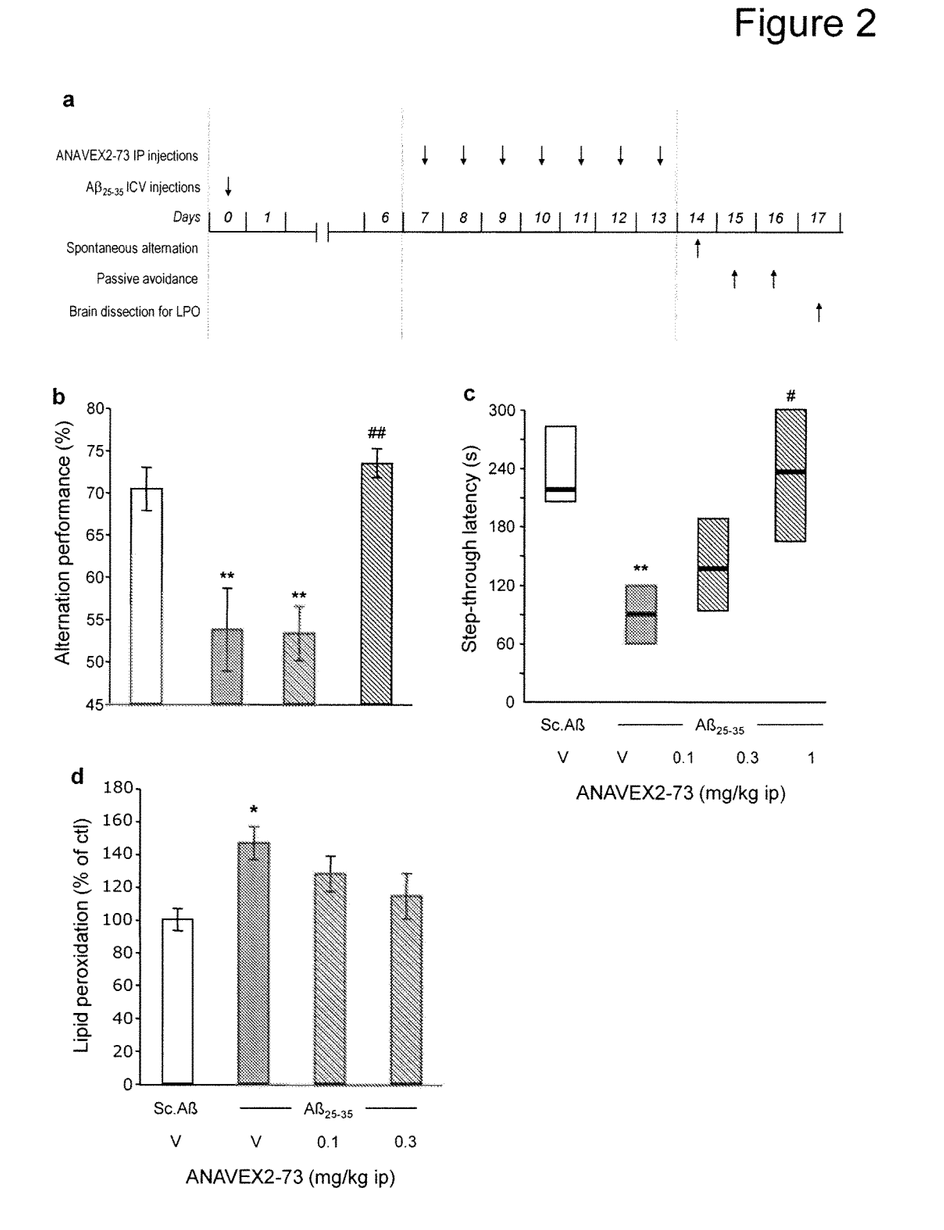
FIG. 2. Delayed administration of ANAVEX2-73 allowed significant attenuations of $A\beta_{25-35}$-induced learning deficits and toxicity. (a) Administration schedule; (b) Y-maze test; (c) passive avoidance response and (d) lipid peroxidation measure.
Figure 3:
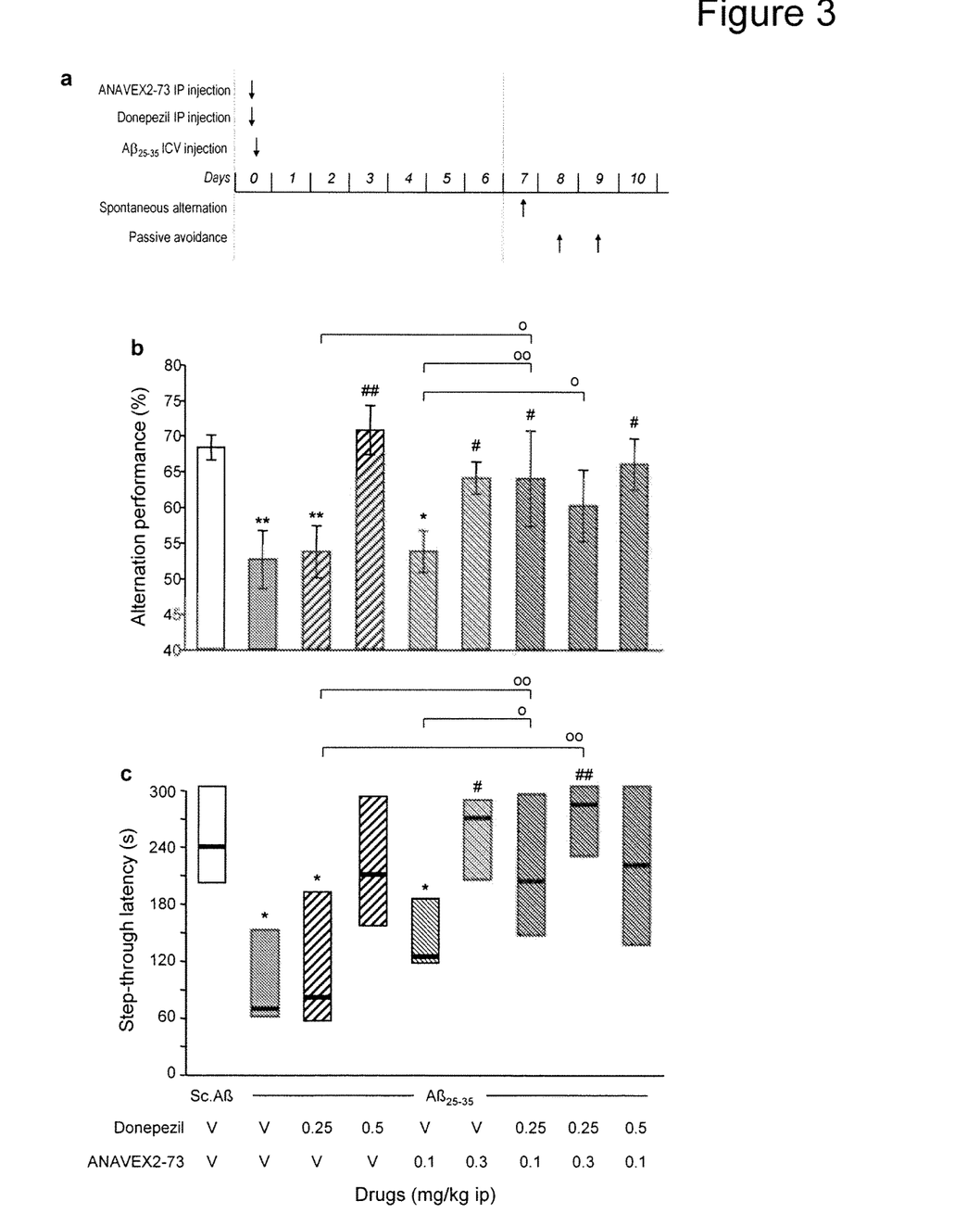
FIG. 3. Combination of ANAVEX2-73 with donepezil showed synergistic effects on the prevention of $A\beta_{25-35}$-induced learning deficits. (a) Administration schedule, (b) Y-maze test; (c) passive avoidance response. Administration schedule: mice received ANAVEX2-73 (0.1, 0.3 mg/kg i.p.) and/or donepezil (0.25, 0.5 mg/kg i.p.) once 20 min before $A\beta_{25-35}$ (9 nmol i.c.v.) at day 0. Animals were examined between days 7 and 9. $F_{(8,131)}=15.1$, $p<0.0001$ in (b); $H=34.1$, $p<0.0001$ in (c); n=11-18 per group. *$p<0.05$, **$p<0.01$ vs. the Sc.A$\beta$/V-treated group; # $p<0.05$, ## $p<0.01$ vs. the $A\beta_{25-35}$/V-treated group; o $p<0.05$, oo $p<0.01$ vs. the designed groups; Dunnett's test in (b); Dunn's test in (c).
Figure 4:
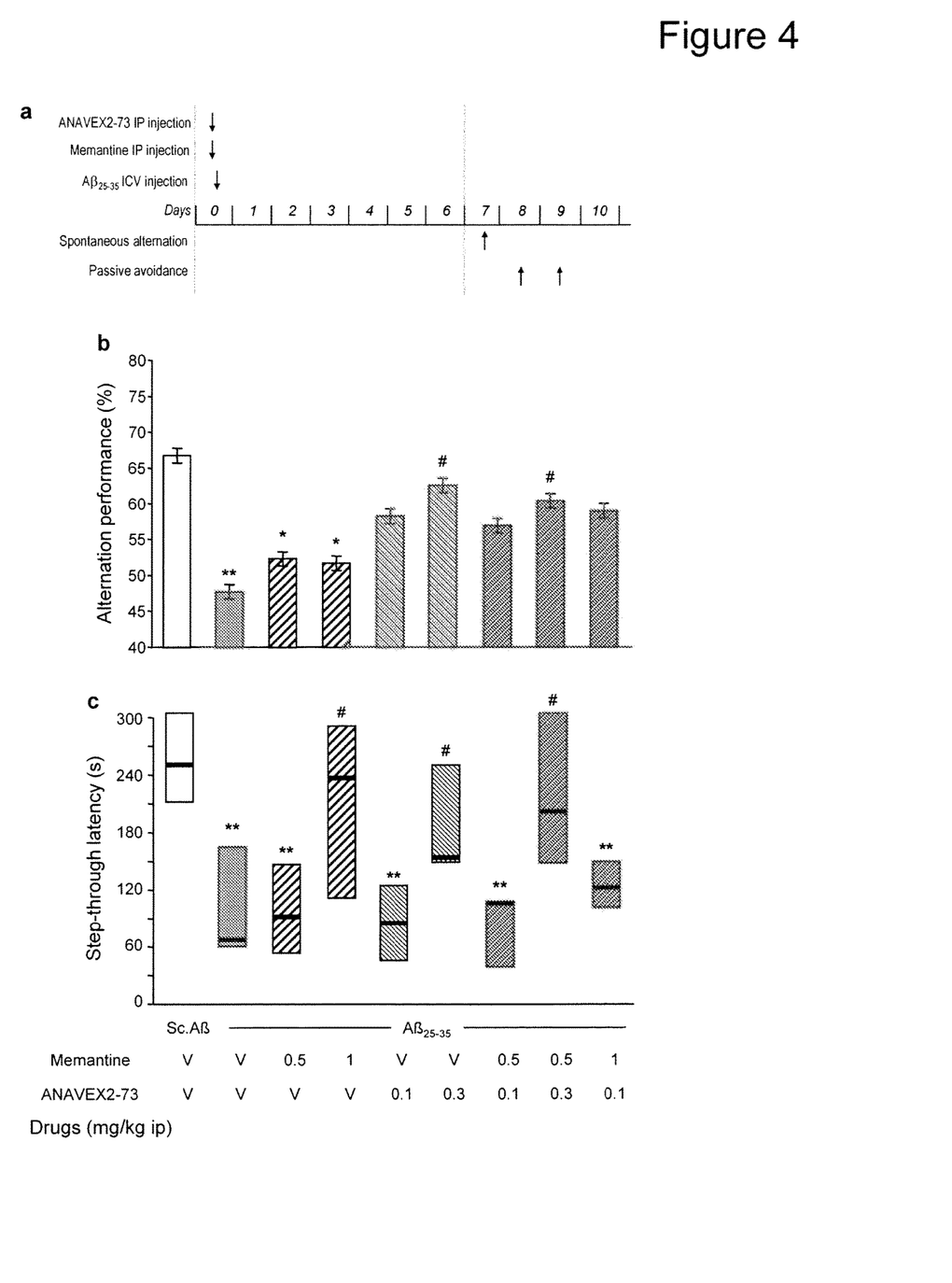
FIG. 4. Combination of ANAVEX2-73 with memantine failed to show additive effects on the prevention of $A\beta_{25-35}$-induced learning deficits. (a) Administration schedule, (b) Y-maze test; (c) passive avoidance response. Administration schedule: mice received ANAVEX2-73 (0.1, 0.3 mg/kg i.p.) and/or memantine (0.5, 1 mg/kg i.p.) once 20 min before $A\beta_{25-35}$ (9 nmol i.c.v.) at day 0. Animals were examined between days 7 and 9. $F_{(8,85)}=3.18$, $p<0.01$ in (b); $H=30.9$, $p=0.0001$ in (c); n=8-18 per group. *$p<0.05$, **$p<0.01$ vs. the Sc.A$\beta$/V-treated group; # $p<0.05$, ## $p<0.01$ vs. the $A\beta_{25-35}$/V-treated group; o $p<0.05$, oo $p<0.01$ vs. the designed groups; Dunnett's test in (b,c); Dunn's test in (c).
Figure 5:
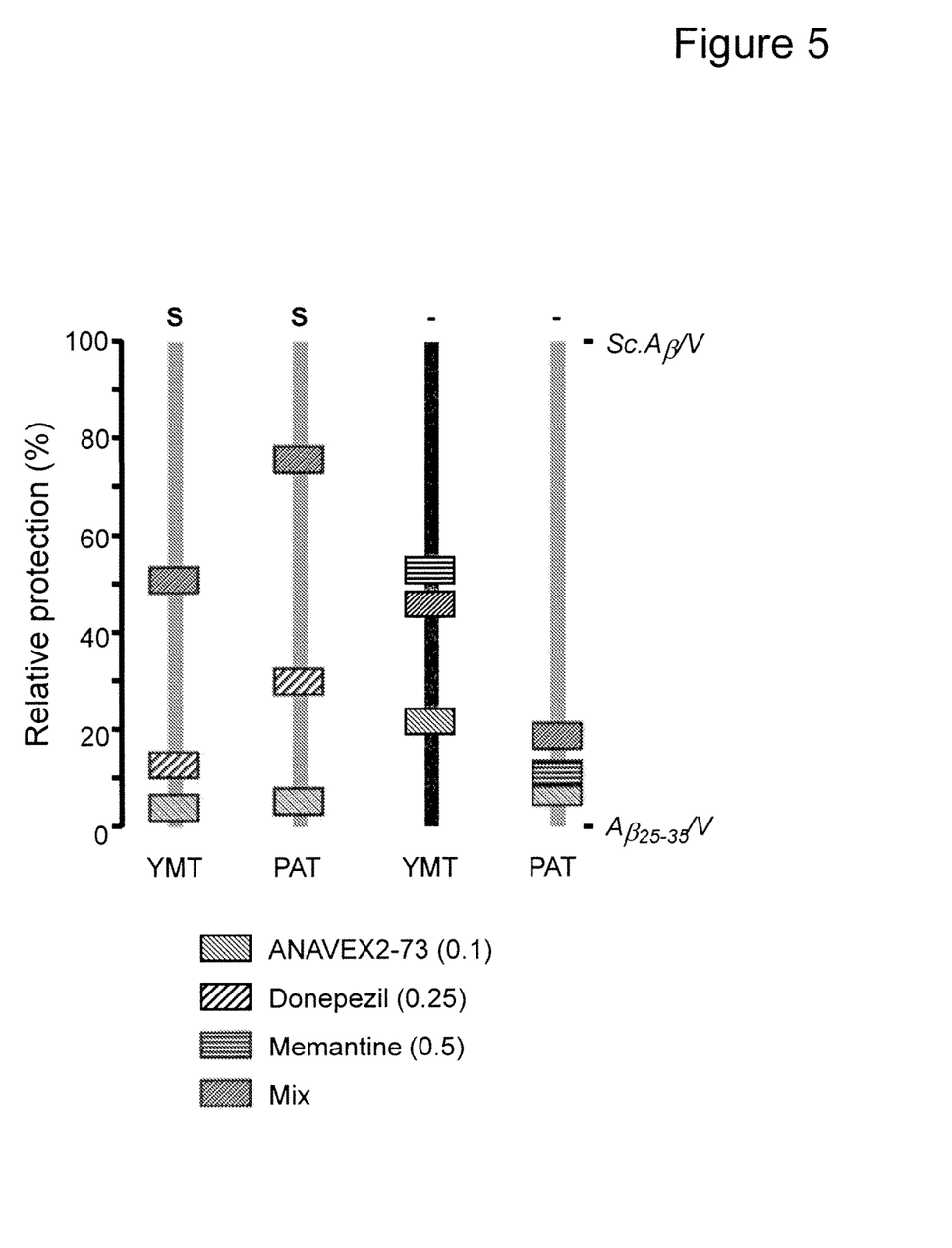
FIG. 5. Cursor-on-scale representation of the relative protection induced by ANAVEX2-73 and donepezil or memantine, and their combination (Mix) in $A\beta_{25-35}$ treated mice. The spontaneous alternation (YMT) and passive avoidance (PAT) responses are shown. Data are from FIG. 3 and FIG. 4. The 100% protection level represents the Sc.A$\beta$/V group and the 0% level, the $A\beta_{25-35}$/V group. Only the data with the lowest doses tested are shown. Synergistic effect of the mix (S) was calculated from the isobologram representation of the data.

The combination of ANAVEX2-73 with actual treatments of Alzheimer's dementia (AD) and, particularly including co-therapy with either donepezil or memantine, was tested. A clear synergic effect with donepezil (as illustrated on FIG. 5) was established. The lack of additive effect with memantine (see also FIG. 5) suggested that the mechanism of action of the compounds are markedly different and therefore that neither the muscarinic M1 agonism nor the $\sigma_1$ receptor agonism are able, under these administration conditions to impact the pharmacological action of mematine, i.e., the partial NMDA receptor blockade.

The anti-amnesic and neuroprotective effect of ANAVEX2-73 against amyloid toxicity is effective in pre- and post-protection, meaning when the drug is administered before of after the amyloid peptide challenge, and the combination with donepezil boosts the therapeutic efficacy of each drug.

EXAMPLE 1

Neuroprotection Against Beta Amyloid

A 67 year old male diagnosed with early stage Alzeheimer's dementia is treated with 10 mg of A2-73 and a sub-MAD dosage of 3 mgs donepezil, once per week for three years. His mental function is tested quarterly and does not decrease over the period. On autopsy his brain is found to contain senile plaques but very low content in amyloid peptide oligomers.

EXAMPLE 2

Neuroprotection Against Oxidative Stress

A 29 year old female balloonist, anticipating anoxic stress, is orally administered 10 mgs of A2-73 and 5 mgs donepezil, daily for 5 days preceeding a ballon ascent. The ballonist ascends to 6,000 meters without oxygen assist and suffers no anoxic damage.

EXAMPLE 3

Neuroprotection Against Neurotoxicity

A 37 year old male hazardous materials engineer, anticipating neurotoxic stress stress, is orally administered 1 mg of A2-73 and 3 mgs galantamine, daily for 5 days preceeding exposure to tetanus toxin. The engineer is exposed 0.1 ng/kg of said neurotoxin and suffers no damage.

EXAMPLE 4

Neuroprotection in Stroke Patient

A 57 year old male enters the emergency room and is diagnosed with an ischemic event involving the middle cerebral artery, with symptomatology onset being under 1 hr. Immediately, the patient is administered an i.v. supplemented with 1 mg of A2-73 and 3 mgs rivastigmine, while blood supply to the restricted area is restored. Daily testing of cognitive and motor systems show no deficits in physical or mental capacities. In addition, CT/MRI imaging show no signs of lesioning in the affected region, immediately following recovery and that this was maintained and confirmed by follow-up imaging and behavior testing.

EXAMPLE 5

Neuroprotection Against Amyloid

An 80 year old female patient is diagnosed with AD and treated with donepezil 10 mg daily for 3 yrs without. The medication is switched to daily donepezil 3 mg and A2-73 0.5 mg in a combination dosage form. The patients cognitive score stabilizes and then increases slowly and regularly over the following months.

Dosing Information/Dosage Forms:

For Anavex2-73 dosages of about 0.01-100 mg/daily, preferably 0.5-10 mg/daily, more preferably 0.5-2 mg/daily. Dosing once every two days (3 times a week) is noted. AD is a chronic disease, so staring treatment promptyl with diagnosis is preferred.

For dosages of donepezil, galantamine, rivastigmine, and memantinedonepezil, galantamine, rivastigmine used in combination with A2-73. In some embodiments, these may be administered in sub-MAD (MAD=minimum active dose) doses.

Particular attention is drawn to the method of this invention comprising A2-73 administration and administration of at least one cooperating acetylcholinesterase inhibitor (donepezil, galantamine, rivastigmine, or memantine), wherein at least one of said therapeutically effective amounts of either A2-73 or the dose of cooperating acetylcholinesterase inhibitor is sub-therapeutic (sub-MAD) as compared to the active dose when used alone. Either the A2-73 or the cooperating acetylcholinesterase inhibitor is used in sub-MAD amount or both are. While this does not exclude more than one cooperating acetylcholinesterase inhibitor being used in treatment of a single subject, it is contemplated that particular embodiments will consist of A2-73, and a single cooperating acetylcholinesterase inhibitor, wherein one or both drugs are administered in sub-MAD amounts. Non-limiting useful doses for A2-73 combination therapy are as follows:

Donepezil 1-3 mg/day or 5 mg once every two days.
Rivastigmine 1 mg/day.
Galantamine 8-10 mg/day once a day.

Memantine 1-5 mg/day.

Reported dosages of donepezil shown to be effective in controlled clinical trials of the treatment of mild to moderate Alzheimer's disease are 5 mg or 10 mg administered orally once per day. Dosages up to about 23 mg/day are also noted.

Reported dosages of galantamine are about 8 to 16 mg twice daily. Note is made of dosage range from about 0.5 to about 8 mg, and optionally from about 1 to about 6 mg.

Reported rivastigamine dosages begin with about 1.5 mg orally twice a day with morning and evening meals. After about two weeks of treatment, it is increased to about 3 mg twice a day. Subsequent increases to 4.5 mg and 6 mg twice a day are noted. Rivastagmine is notably useful in transdermal patch. A useful initial patch dose: 4.6 mg/24 hours, but a range of 1-8 mg is noted. In some embodiments a maintenance patch dose after about four weeks of treatment is increased from about 8-16 mg, and particularly, 9.5 mg/24 hours for as long as this dose is beneficial. The dose can then be increased to about 9-20 mg and particularly about 13.3 mg/24 hours.

Reported memantine dosing is initial about 5 mg orally once daily, then titrated upwards by 5 mg per week. Reported Maintenance: 5 mg once daily up to 10 mg twice daily. are noted. Useful doses are from about 0.5 to about 20 mg.

Dosing for donepezil, galantamine, rivastigmine, or memantine may be daily, but further include from twice daily to every other day, to once per week or less frequently. Of course, transdermal dosing is also a continuous dosing. The pharmacologically active compositions of this invention can be processed in accordance with conventional methods of Galenic pharmacy to produce medicinal agents for administration to subjects, e.g., mammals including humans.

The compositions of this invention individually or in combination are employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules, vials, and injector cartridges are convenient unit dosages.

"Unit dosage form" shall mean single drug administration entity. By way of example, a single tablet, capsule, dragee, or trochee, suppository, or syringe combining both A2-73 and at least one of consisting of donepezil, galantamine, rivastigmine, or memantine.

Also for parenteral application, particularly suitable are tablets, dragees, liquids, drops, suppositories, or capsules. A syrup, elixir, or the like can be used wherein a sweetened vehicle is employed. Sublingual and buccal forms are also noted.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising 1-100 mg of Anavex2-73 or and 0.5 to 5 mg of donepezil or other cooperating acetylcholinesterase in a pharmaceutically acceptable carrier per unit dosage.

Specific mention is made of various dosing regiments. "Co-timely" as to drug administration shall mean administration of at least one second drug (consisting of donepezil, galantamine, rivastigmine, or memantine) while a A-273 is present in a therapeutically effective amount. It is to be understood that in some instances this will require sequential administration. In some instances, and without limitation, multiple routes of administration will be employed such as intravenous or subcutaneous injection as well as orally.

"Coordinated" dosing in the practice of the present invention combining A2-73 and one second drug (consisting of donepezil, galantamine, rivastigmine, or memantine) shall mean administration of an A2-73 such that effective plasma levels of the A2-73 will be present in a subject during the period when said second drug is present at an effective level. In some embodiments this will be about 0.5 to about 12 hours after A2-73 has been administered.

The invention claimed is:

1. A dosage form comprising a therapeutically neuroprotective amount of A2-73 of about 0.1 mg/kg and a neuroprotective amount of the cooperating acetylcholinesterase inhibitor donepezil of about 0.25 mg/kg.

2. The dosage form of a therapeutically neuroprotective amount of A2-73 and a neuroprotective amount of the cooperating acetylcholinesterase inhibitor donepezil wherein said therapeutically neuroprotective amounts of A2-73: donepezil are present at a ratio of about 2:5 by weight.

* * * * *